(12) United States Patent
Twomey et al.

(10) Patent No.: US 7,261,719 B1
(45) Date of Patent: Aug. 28, 2007

(54) FEMORAL SIZING APPARATUS AND METHOD

(75) Inventors: R. Scott Twomey, Fort Wayne, IN (US); Robert G Metzger, Wakarusa, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 414 days.

(21) Appl. No.: 10/701,272

(22) Filed: Nov. 4, 2003

(51) Int. Cl.
*A61B 17/58* (2006.01)
*A61B 17/60* (2006.01)
*A61F 2/00* (2006.01)

(52) U.S. Cl. .................... 606/102; 606/88

(58) Field of Classification Search ........... 600/587; 606/102, 86, 87, 88, 89, 96; 33/511, 512
See application file for complete search history.

(56) References Cited

U.S. PATENT DOCUMENTS

| | | | |
|---|---|---|---|
| 5,486,178 A | | 1/1996 | Hodge |
| 5,562,675 A | | 10/1996 | McNulty et al. |
| 5,569,261 A | * | 10/1996 | Marik et al. ............. 606/88 |
| 5,624,444 A | * | 4/1997 | Wixon et al. ............. 606/88 |
| 5,662,656 A | * | 9/1997 | White ..................... 606/88 |
| 5,688,279 A | * | 11/1997 | McNulty et al. .......... 606/88 |
| 5,688,280 A | * | 11/1997 | Booth et al. ............. 606/88 |
| 5,720,752 A | * | 2/1998 | Elliott et al. ............ 606/88 |
| 5,810,831 A | * | 9/1998 | D'Antonio ............... 606/88 |
| 6,056,756 A | * | 5/2000 | Eng et al. ............... 606/87 |
| 6,077,270 A | * | 6/2000 | Katz ..................... 606/88 |
| 6,096,043 A | * | 8/2000 | Techiera et al. ......... 606/88 |
| 6,290,704 B1 | * | 9/2001 | Burkinshaw et al. ...... 606/88 |
| 6,558,391 B2 | * | 5/2003 | Axelson et al. .......... 606/88 |

OTHER PUBLICATIONS

"AGC Traditional Surgical Overview", copyright 2001 Biomet Orthopedics, Inc.

* cited by examiner

*Primary Examiner*—Max F. Hindenburg
*Assistant Examiner*—Michael Apanius
(74) *Attorney, Agent, or Firm*—Harness, Dickey & Pierce, P.L.C.

(57) ABSTRACT

A sizing apparatus for determining the anterior-posterior size of a distal end of a femur. The apparatus includes a block having a face engageable with the distal end of the femur, and a body mounted on the block and slidable relative to the block in a medial-lateral direction. A stylus is mounted on the body.

21 Claims, 3 Drawing Sheets

FEMORAL SIZING APPARATUS AND METHOD

FIELD OF THE INVENTION

The present invention relates to an apparatus and method for femoral sizing.

BACKGROUND OF THE INVENTION

Knee replacement surgery is currently performed with a view toward minimizing joint exposure by applying small incision procedures, also known as minimally invasive procedures. To obtain consistent results and aid the surgeon in such procedures, new instrumentation adapted to the smaller incision size is advantageous.

One of the important steps in knee replacement surgery is sizing correctly the femoral component and, in particular, accurately determining the anterior-posterior dimension of the resected distal femur. Several types of femoral sizers are currently available for this purpose. Nevertheless, femoral sizers that avoid soft tissue impingement and are well-suited to small-incision procedures are still desirable.

SUMMARY OF THE INVENTION

One embodiment of the invention provides a sizing apparatus for determining the anterior-posterior size of a distal end of a femur. The apparatus includes a block having a face engageable with the distal end of the femur, and a body mounted on the block and slidable relative to the block in a medial-lateral direction. A stylus is mounted on the body.

Another embodiment provides a sizing apparatus for determining the anterior-posterior size of a distal end of a femur. The apparatus includes a block, a body, and a stylus. The block has an upper portion and a lower portion. The upper portion includes a U-shaped member with two pads engageable with the distal end of the femur, and a rod extending between the pads in the medial-lateral direction. The lower portion includes a surface engageable with the distal end of the femur, and a base. The body is slidably mounted on the rod and is slidably supported on the base of the block for movement in the medial-lateral direction. The body has a longitudinal bore and a window opening. The stylus includes a shaft slidably received in the bore for movement in an anterior-posterior direction. The shaft has an indicator viewable through the window opening.

Yet another embodiment of the invention provides a sizing apparatus for determining the anterior-posterior size of a distal end of a femur. The apparatus includes a block having a face and a base, a body mounted on the base for movement relative to the block in the medial-lateral direction, and a stylus mounted on the body. The face of the block engages the distal end of the femur.

Another embodiment of the invention provides a method for determining a size of a distal femur. The method includes providing a sizing apparatus having a block, a body slidably mounted on the block in the medial-lateral direction and a stylus received in a bore of the block. The method includes attaching a face of the block to the distal femur and selectively sliding the body relatively to the block in a medial-lateral direction. The method further includes moving the stylus to bring a tip of the stylus in contact with an anterior surface of the distal femur, and observing an indicator on the stylus through a window opening in the body.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiments is merely exemplary in nature and is in no way intended to limit the invention, its application, or uses. Although embodiments of the invention are described below in the context of a resected distal femur, such description is merely illustrative, and the invention is not so limited. It will be appreciated that the invention can be equally practiced in connection with the distal end of any bone.

Figure 1:
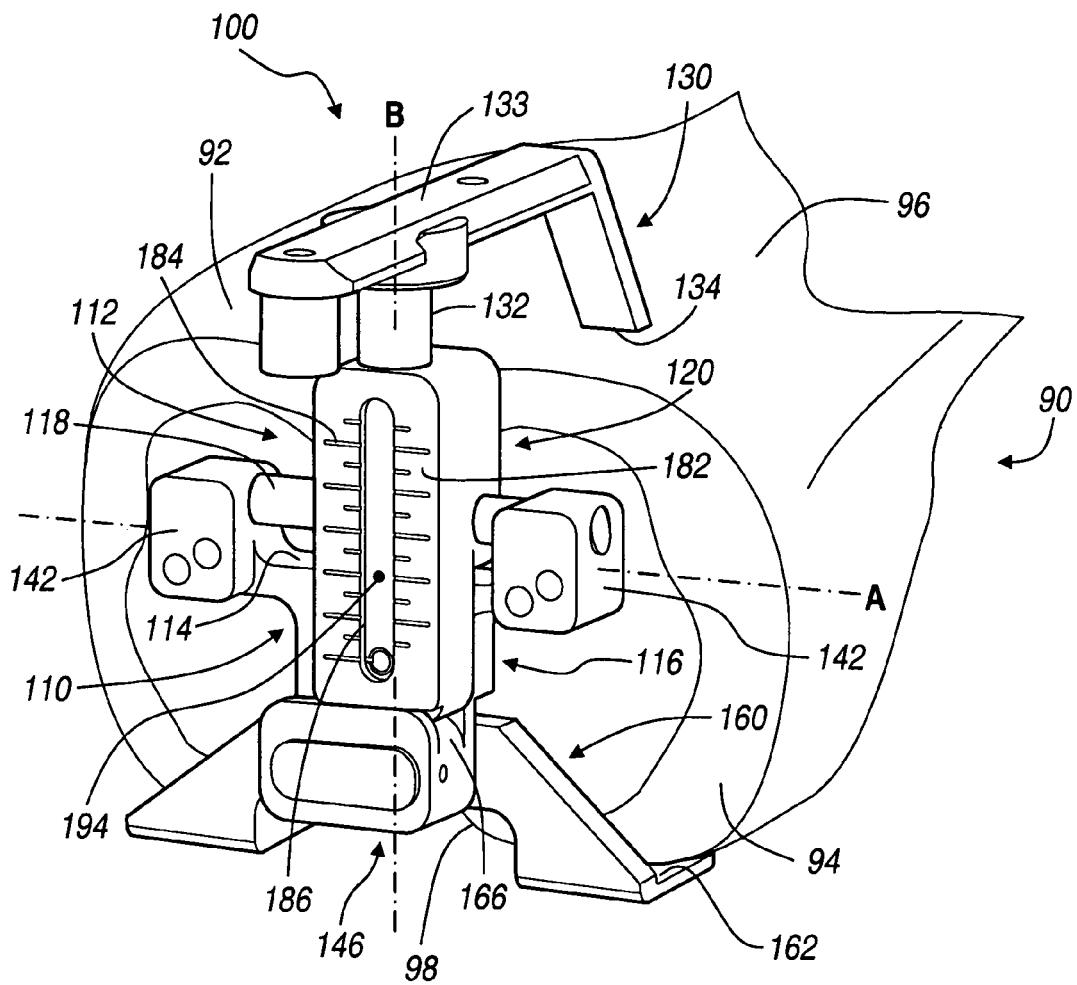
FIG. 1 is a front perspective view of an embodiment of a sizing apparatus according to the invention, with a body shown in a first position.
Figure 2:
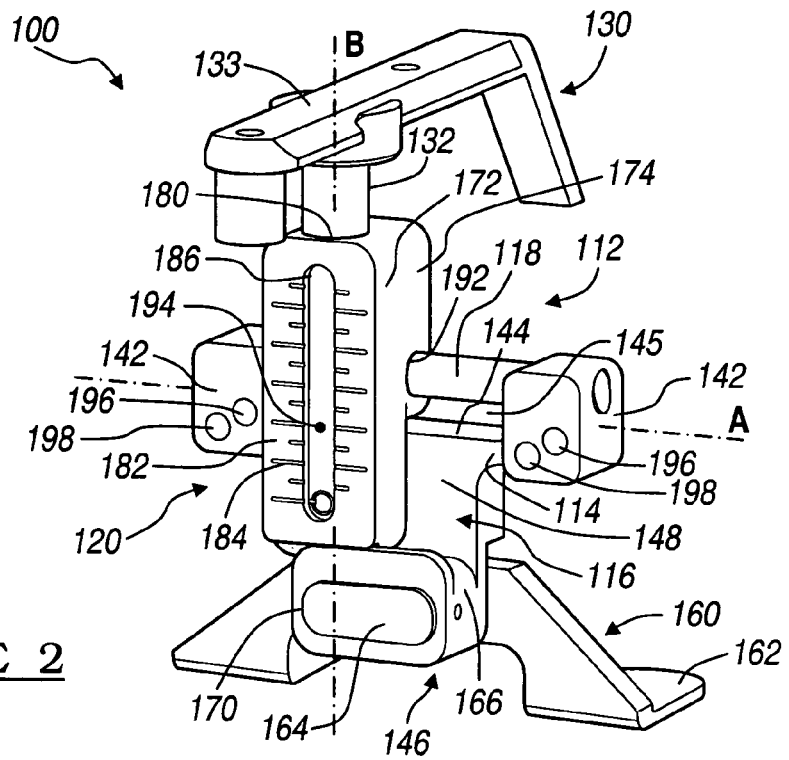
FIG. 2 is a front perspective view of the sizing apparatus of FIG. 1, with the body shown in a second position.
Figure 3:
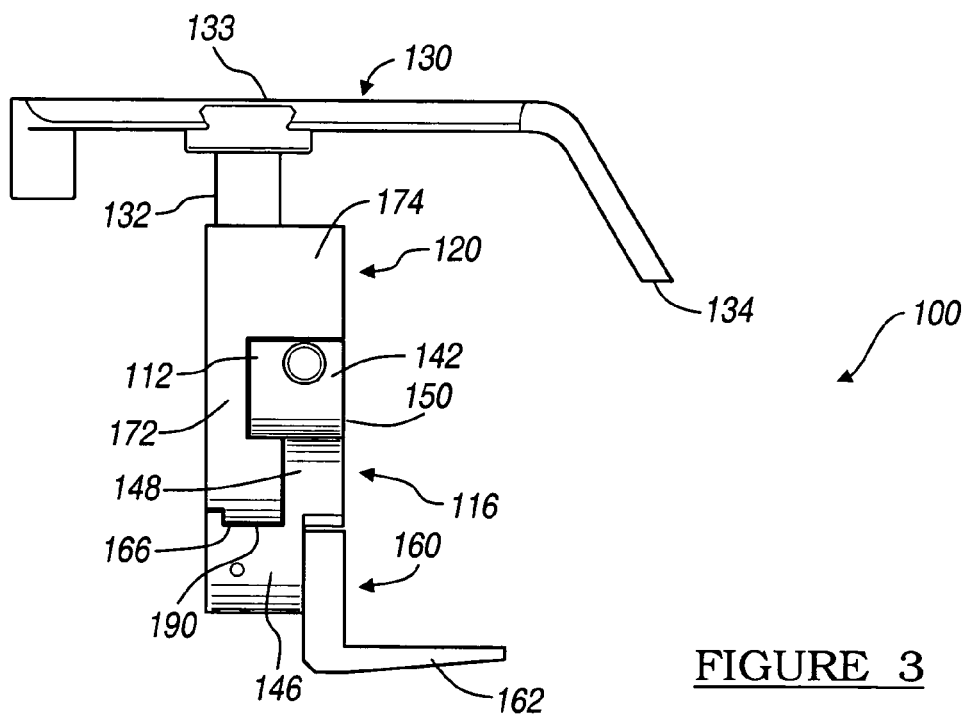
FIG. 3 is a side elevational view of the sizing apparatus of FIG. 1.
Figure 4:
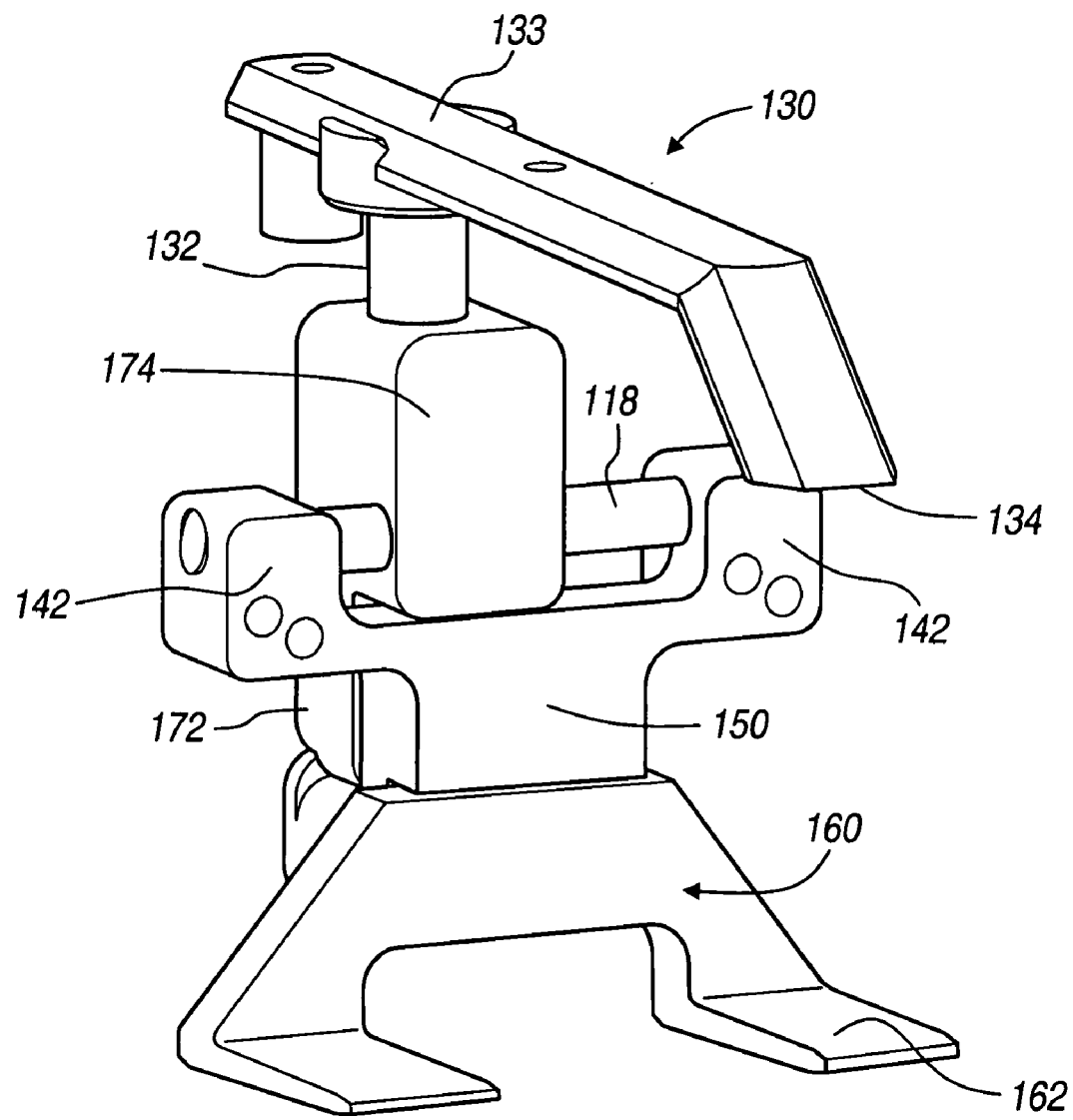
FIG. 4 is a rear perspective view of the sizing apparatus of FIG. 1.

An embodiment of a femoral sizing apparatus 100 according to the invention is illustrated in FIGS. 1-4. The sizing apparatus 100 includes a block 110, a body 120 and a stylus 130. The block 110 has an upper portion 112 and a lower portion 116. The upper portion 112 includes a U-shaped member 114 having two pads 142. A rod 118 extends between the pads 142, providing a clearance 145 between the rod 118 and a surface 144 of the upper portion 112. The rod 118 may be modularly connected to the pads 142 such that the rod 118 can be detached and re-attached to the block 110 by methods known in the art, such as removable fasteners, press-fitting, taper connections, etc. As best seen in FIG. 3, the pads 142 and lower portion 116 define an engagement surface 150 that is operable to contact and engage the resected surface 94 of the distal end 92 of a femur 90 for anterior-posterior sizing of the femur 90. The anterior-posterior direction is indicated by an axis "B". The lower portion 116 of the block 110 includes a web 148 at a right angle with a base 146. The base 146 is adapted to engage modularly with a support 160 that includes feet 162. In one embodiment, the base 146 defines an opening 170 that receives an extension 164 of the support 160. Alternatively, the support 160 may be integral with the base 146. The support 160 may be stationary relative to the base 146, or may be pivotably connected to the base 146. The feet 162 provide a surface that is placed in contact with the posterior surface 98 of the distal end 92 of the femur 90 during the sizing procedure. The base 146 defines a U-shaped channel 166 adjacent to the web 148.

The body 120 includes first and second portions 172, 174 that can be arranged to form an L-shaped profile. The first portion 172 includes a longitudinal bore 180 and a front face 182 on which a calibrated scale 184 may be marked, or imprinted, or otherwise affixed. A longitudinal window opening 186 on the front face 182 of the first portion 172 adjacent to the markings of the scale 184 provides a view of the bore 180. The first portion 172 includes a projection 190 that is received in the channel 166 for slidable contact thereon. The second portion 174 includes a through-hole 192 receiving the rod 118.

The first portion 172 of the body 120, the bore 180 and the window opening 186 extend along the anterior-posterior direction when the sizing apparatus 100 is attached to the distal end 92 of the femur 90, such that the feet 162 are in contact with the posterior surface 98. The rod 118 extends in the medial-lateral direction indicated by an axis "A". When the sizing apparatus 100 is so positioned, the body 120 can slide along the rod 118 along the track defined by the channel 166.

The stylus 130 includes a shaft 132 and an arm 133 terminating in a stylus tip 134. The shaft 132 is slidably received in the longitudinal bore 180 of the first portion 172 of the body 120 and is movable along the bore 180. The arm 133 can rotate about the bore 180 with the shaft 132 or relatively to the shaft 132, such that the stylus tip 134 can be brought in contact with any point on the anterior surface 96 for determining the size of the distal end 92 of the femur 90. The shaft 132 may include on its surface an indicator 194, which is visible through the window opening 186 and provides a size reading on the scale 184 when the stylus tip 134 contacts the anterior surface 96 of the femur 90. The stylus 130 can slide axially with the body 120 in the medial-lateral direction along the rod 118 to prevent soft tissue impingement during sizing, especially in the anterior lateral corner, and to provide working space and clearance especially during small incision knee procedures. FIGS. 1 and 2 illustrate the body 120 in two different positions relatively to the block 110 along the medial-lateral direction. For left knee surgery, for example, the body 120 is displaced to the medial position illustrated in FIG. 1. For right knee surgery, the body 120 is displaced to the medial position shown in FIG. 2.

Each pad 142 may include pre-drilled holes 196 for preparing fixation holes in the distal end 92 of the femur 90. Other pre-drilled holes 198 may be used for pinning the sizing apparatus 100 to the distal end 92. The body 120 may be displaced in the medial-lateral direction to provide clearance while preparing the fixation holes on the femur 90 or while affixing the sizing apparatus 100 to the femur 90.

In operation, after the distal end 92 is resected, the sizing apparatus 100 is attached to the distal end 92, such that the feet 162 are engaged in direct contact with the posterior surface 98 and the engagement surface 150 of the block 120 is in direct contact with the resected surface 94 of the femur 90. The body 120 is slid relatively to the block 110 in the medial-lateral direction as needed or depending on whether the operation is for the right or left knee, to avoid tissue impingement during sizing. The arm 133 of the stylus 130 is rotated, such that the stylus tip 134 contacts the anterior surface 96. Several readings may be taken on the scale 184 as the stylus tip 134 moves about the anterior surface 96 by observing the position of the indicator 194 relative to the scale 184. The size of the femur 90 is determined by the highest reading on the scale 184. During the movement of the stylus 130, the body 120 may be moved medially or laterally to accommodate the movement of the stylus 130 without causing tissue impingement.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A sizing apparatus for determining the anterior-posterior size of a distal end of a femur comprising:
   a block having a face engageable with the distal end of the femur, the block having an upper portion including a U-shaped member with two pads engageable with the distal end of the femur, and a rod extending between the pads in a medial-lateral direction, the block having a base spaced apart from the rod;
   a body having a longitudinal bore, the body slidably mounted on the rod relative to the block in a medial-lateral direction, the rod passing through an aperture of the body, the body having a lower surface slidably contacting an upper surface of the base of the block; and
   a stylus having a shaft coupled to the longitudinal bore of the body and moveable in an anterior-posterior direction along the bore.

2. The sizing apparatus of claim 1, further comprising a support connected to the block and engageable with a posterior surface of the distal end of the femur.

3. The sizing apparatus of claim 1, wherein the stylus includes an arm attached to the shaft, the arm having a stylus tip.

4. The sizing apparatus of claim 1, wherein the body defines a window opening through which a portion of the shaft is visible.

5. The sizing apparatus of claim 4, wherein the shaft includes an indicator providing a reading on a scale affixed to the body adjacent the window opening.

6. The sizing apparatus of claim 1, wherein the lower surface of the body is slidably received in a U-shaped channel of the base.

7. The sizing apparatus of claim 1, wherein the base is modularly connected with a support adapted to contact a posterior surface of the femur.

8. A sizing apparatus for determining the anterior-posterior size of a distal end of a femur, the apparatus comprising:
   a block having an upper portion and a lower portion, wherein the upper portion includes a U-shaped member with two pads engageable with the distal end of the femur, and a rod extending between the pads in the medial-lateral direction, and wherein the lower portion includes a surface engageable with the distal end of the femur, and a base;
   a body slidably mounted on the rod and slidably supported on the base of the block for movement in the medial-lateral direction, the body having a longitudinal bore and a window opening; and
   a stylus having a shaft slidably received in the bore for movement in an anterior-posterior direction.

9. The sizing apparatus of claim 8, wherein the base is coupled to a support that is adapted to contact a posterior surface of the femur.

10. The sizing apparatus of claim 9, wherein the base includes an opening modularly connected with an extension of the support.

11. The sizing apparatus of claim 9, wherein the base is integral with the support.

12. The sizing apparatus of claim 8 wherein the rod is modularly connected to the pads.

13. The sizing apparatus of claim 8, wherein the body includes a scale adjacent to the window opening.

14. A sizing apparatus for determining the anterior-posterior size of a distal end of a femur, the apparatus comprising:

a block having a face engageable with the distal end of the femur, the block having an upper portion including a U-shaped member with two pads engageable with the distal end of the femur, a rod extending between the pads in the medial-lateral direction, and a lower portion having a base, the base being spaced apart from the rod;

a body having a lower surface slidably mounted on the base, the body having an aperture slidably receiving the rod, the body slidably contacting both the rod and the base and moveable relative to the block in the medial-lateral direction; and a stylus mounted on the body.

15. The sizing apparatus of claim 14, wherein the body is slidably engaged with a channel defined by the base.

16. The sizing apparatus of claim 15, wherein the channel is U-shaped.

17. The sizing apparatus of claim 14, wherein the face of the block is engageable with a resected surface of the distal end of the femur.

18. A method for determining a size of a distal femur, the method comprising:

providing a sizing apparatus having a block, the block including a U-shaped member with two pads engageable with the distal end of the femur, a rod extending between the two pads in a medial-lateral direction, and a base, a body slidably mounted on the block in the medial-lateral direction and a stylus extending from a bore of the body, the bore extending in an anterior-posterior direction;

engaging a face of the block to the distal femur;

selectively sliding the body along the rod in the medial-lateral direction;

sliding a lower surface of the body along an upper surface of the base selectively in the medial-lateral direction;

moving the stylus to bring a tip of the stylus in contact with an anterior surface of the distal femur; and observing an indicator associated with the movement of the stylus.

19. The method of claim 18, wherein the indicator may be observed through a window opening in the body.

20. The method of claim 18, further comprising reading the size of the distal femur on a scale affixed to the body at a position of the indicator.

21. The sizing apparatus of claim 8, wherein the shaft includes an indicator viewable through the window opening.

* * * * *